United States Patent [19]
Ratcliff et al.

[11] Patent Number: 6,136,348
[45] Date of Patent: Oct. 24, 2000

[54] COMPOUND AND METHOD FOR DEGRADING AMINO ACIDS

[76] Inventors: Perry A. Ratcliff, 7439 E. Lincoln Dr., Scottsdale, Ariz. 85253; Edward J. Lynch, 90 South Croxted Road, West Dulwich, SE21 8BD, United Kingdom

[21] Appl. No.: 09/205,997

[22] Filed: Dec. 4, 1998

Related U.S. Application Data

[60] Provisional application No. 60/067,585, Dec. 5, 1997.

[51] Int. Cl.[7] ........................... A61K 33/14
[52] U.S. Cl. ........................... 424/661
[58] Field of Search ........................... 424/661

[56] References Cited

PUBLICATIONS

Article entitled "Protein Synthesis", Chapter 27, *Biochemistry*, Second Edition, by Lubert Stryer, Stanford University, W.H. Freeman and Company, San Francisco, 6 pages.

"The Inhibitory Effect of Alcide®, An Antimicrobial Drug, On Protein Synthesis in *Escherichia coli*", by JoAnn Scatina and Mohamed S. Abdel–Rahman, *Journal of Applied Technology*, vol. 5, No. 6, 1985, pp. 388–394.

*Primary Examiner*—Raymond Henley, III
*Attorney, Agent, or Firm*—Cahill, Sutton & Thomas P.L.C.

[57] ABSTRACT

Amino acids and glycoproteins are effectively removed in an infection site or potential infection site by application of an aqueous solution or other vehicle such as a gel or salve of chlorine dioxide to inhibit the growth of microorganisms resulting in reduction of numbers of infection causing microorganisms and treatment of the attendant infection.

7 Claims, 1 Drawing Sheet

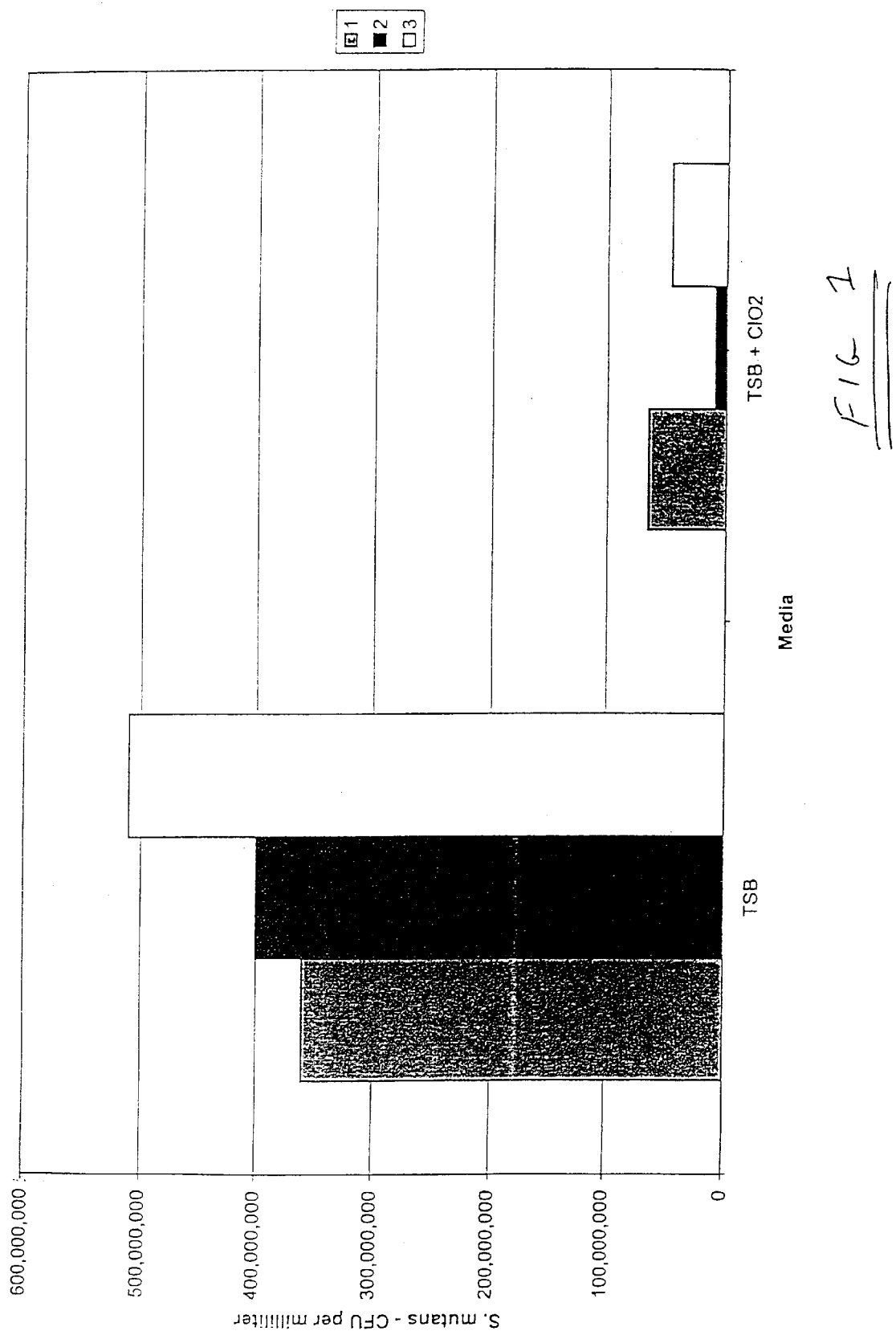

COMPOUND AND METHOD FOR DEGRADING AMINO ACIDS

CROSS-REFERENCE TO RELATED APPLICATIONS

The present application contains subject matter disclosed in and claims priority to a provisional application entitled "COMPOUND AND METHOD FOR DEGRADING AMINO ACIDS, assigned Ser. No. 60/067,585, filed Dec. 5, 1997.

BACKGROUND OF THE INVENTION

1. Field of the Invention

The present invention relates to degradation of amino acids and, more particularly, to a chlorine dioxide compound for degrading amino acids.

2. Description of Related Art

There are common molecular patterns and principles that underlie the diverse expressions of life. Organisms as different as the bacterium *escherichia coli* and humans have many common features at the molecular level. They use the same building blocks to construct macromolecules. The flow of genetic information from deoxyribonucleic acid (DNA) to ribonucleic acid (RNA) to protein is essentially the same in both species. Both use adenosine triphosphate (ATP) as a currency of energy.

All life is a combination of many molecules of different structural formations. A molecule is defined as a combination of two or more atoms. These may be similar atoms such as the combination of two oxygen atoms to make molecular oxygen, $O_2$. Most molecules consist of two different elements and structural relationships. All atoms carry electrical charges; some are positive and some are negative. The attraction between the positive and the negative electrical forces binds these into stable molecules which make life possible.

Molecules described in a textbook are shown as two-dimensional structural formulae. Actually, these are three-dimensional structures with many convolutions, wherein different portions of these molecules and their electrical charges or valence bonds are exposed to other molecular or atomic forces. The strength of these electrical forces, or valence bonds, are the basis for degrees of stability of all living structures.

The complex molecules of amino acids are structures made up of varying atomic elements, primarily carbon, hydrogen, nitrogen, sulfur and oxygen. The essential amino acids in humans are those that must be obtained from food whereas the balance can be endogenously created. The strength of the electromotive forces of shared valence bonds is directly related to the stability of a given compound. Molecular oxygen will easily break the valence bonds around sulfur atoms or double bonds between other atoms.

A chemical compound such as L. cysteine which contains sulfur, has a valence bond on a terminal arm with one valence bond to a terminal carbon and another valence bond to a terminal hydrogen. It also has a double bond between a terminal carbon and a molecule of oxygen. These are the weak points of cysteine, making it more easily destroyed by oxidative consumption than some of the other amino acids. The high electromotive forces of oxygen can attack these weaker valence areas, breaking up the arms and oxidatively consuming the molecule. Lynch, using 0.1% chlorine dioxide, has documented the oxidative consumption of cysteine and methionine into pyruvate. (Lynch et al., infra)

SUMMARY OF THE INVENTION

Infections are caused by bacteria, fungi and virus forms and an accepted treatment of infections embraces the reduction of these microorganisms. Microorganisms require the presence of amino acids and glycoproteins as building blocks to produce daughter cells. By treating a location of an infection with an aqueous solution of chlorine dioxide, the amino acids and the glycoproteins present will be degraded. Without amino acids or with a reduced presence of amino acids, the growth of microorganism daughter cells will be reduced or curtailed and the infection will be successfully treated.

It is therefore a primary object of the present invention to degrade the presence of amino acids and glycoproteins and inhibit growth of microorganisms at an infection site.

Another object of the present invention is to provide chlorine dioxide in an aqueous solution or other vehicle to deprive microorganisms of proteins as building blocks for producing daughter cells.

Still another object of the present invention is to treat an infection site with an aqueous solution of chlorine dioxide or chlorine dioxide in another vehicle such as a gel to degrade amino acids and glycoproteins and prevent microorganisms from making new proteins.

Yet another object of the present invention is to alter the amino acid milieux of the oral, vaginal and other body cavities.

A further object of the present invention is to remove cellular debris from internal and external tissue surfaces of animals and man.

A still further object of the present invention is to reduce microbial growth upon dental prosthetics and other appliances.

A yet further object of the present invention is to provide an aqueous solution of chlorine dioxide to reduce the growth of microorganisms by degrading amino acids present.

These and other objects of the present invention will become apparent to those skilled in the art as the description thereof proceeds.

BRIEF DESCRIPTION OF THE DRAWING

The present invention will be described with greater specificity with reference to the following figure:

FIG. 1 is a bar chart illustrating the destruction of *S. mutans* in the presence of chlorine dioxide.

DESCRIPTION OF THE PREFERRED EMBODIMENT

Amino Acid Degradation

It is generally accepted that amino acids, in excess of those needed for the synthesis of proteins, cannot be stored. Rather, surplus amino acids are used as metabolic fuel. The alpha amino group is removed and the resulting carbon skeleton is converted into a major metabolic intermediate. Most of the amino groups have surplus amino acids that are converted into urea. Their carbon skeletons are transferred into acetoacetyl co-enzyme A, pyruvate or one of the intermediates of the citric acid cycle. Hence, fatty acids, keto bodies and glucose can be formed from amino acids. These reactions are facilitated by transaminases, also called aminotransferases.

Transaminases catalyze the transfer of the alpha amino group of many alpha amino acids to alpha ketoglutarate to form glutamate, which is then oxidatively deaminated to yield ammonia. Glutamate transaminase, the most important of these enzymes, catalyzes the transfer of an amino group to alpha ketoglutarate. Thus, alpha amino acid plus alpha ketoglutarate can produce or reduce from alpha keto acid plus glutamate.

Alanine transaminase, which is ubiquitous in mammalian tissue, catalyzes the transfer of an amino group to pyruvate. Thus, alpha amino acid from pyruvate will form or reduce from alpha keto acid and alanine. The alanine group in this step can transfer its amino group to alpha keto glutarate to form glutamate. These two transaminases funnel alpha amino groups from a variety of amino acids into glutamate for conversion into ammonia.

Ammonium ion is formed from glutamate by oxidative deamination, catalyzed by glutamate dehydrogenase, which is unusual in being able to utilize either NAD or NADP. This is another step in the use of oxygen in the deamination process.

The following structural formulae of amino acids shows the amount of double bonds plus the presence of sulfur atoms in the formation of some amino acids. These can be used to become building blocks to form protein. However, when in excess and in the presence of oxygen, they can be converted into compounds such as pyruvate or glutamate to enter the citric acid cycle and produce energy.

The $C_3$ Family: Alanine, Serine and Cysteine Are Converted Into Pyruvate

The three-carbon family amino acids, alanine, cerine, cysteine and threonine, are converted to pyruvate by the presence or addition of oxygen.

Pyruvate is the entry point for the three-carbon amino acids: alanine, serine and cysteine. The transamination of alanine directly yields pyruvate:

Alanine+alpha-ketoglutarate⇌pyruvate+glutamate

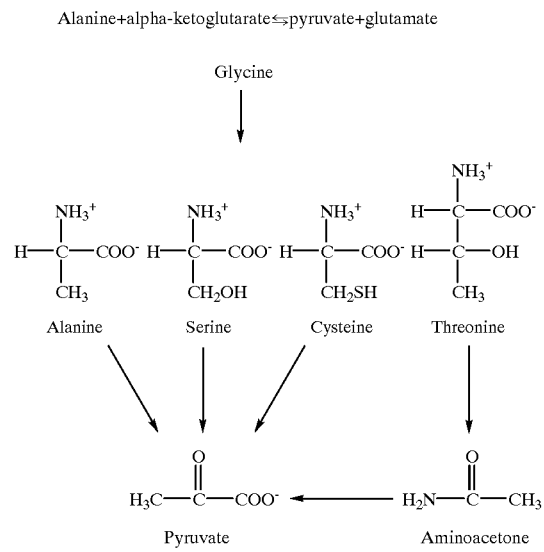

The $C_4$ Family: Aspartate and Asparagine Are Converted Into Oxaloacetate

Aspartate, a four-carbon amino acid, is directly transaminated to oxaloacetate, a citric acid cycle intermediate:

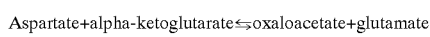

Asparagine is hydrolyzed by asparaginase to $NH_4^+$ and aspartate, which is then transaminated. Aspartate can also be converted into fumarate by the urea cycle. Fumarate is also a point of entry for half of the carbon atoms of tyrosine and phenylalanine.

The $C_5$ Family: Several Amino Acids Are Converted into Alpha-ketoglutarate Through Glutamate The carbon skeletons of several five-carbon amino acids enter the citric acid cycle at alpha-ketoglutarate. These amino acids are converted into glutamate, which is then oxidatively deaminated by glutamate dehydrogenase to yield alpha-ketoglutarate.

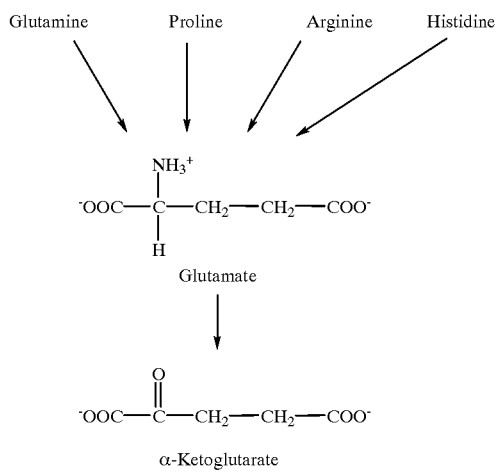

Tryptophan has an aromatic side chain.

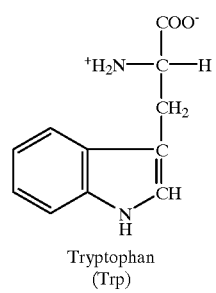

Phenylalanine and Tyrosine Are Degraded by Oxygenases to Acetoacetate and Fumarate The pathway for the degradation of phenylalanine and tyrosine shows how molecular oxygen is used to break an aromatic ring. The first step is the hydroxylation phenylalanine to tyrosine, a reaction catalyzed by the monooxygenase enzyme phenylalanine hydroxylase.

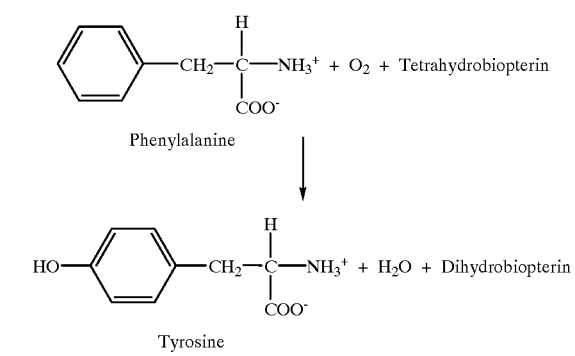

The reductant here is tetrahydrobiopterin, an electron carrier. The oxidized form of this electron carrier is dihydrobiopterin.

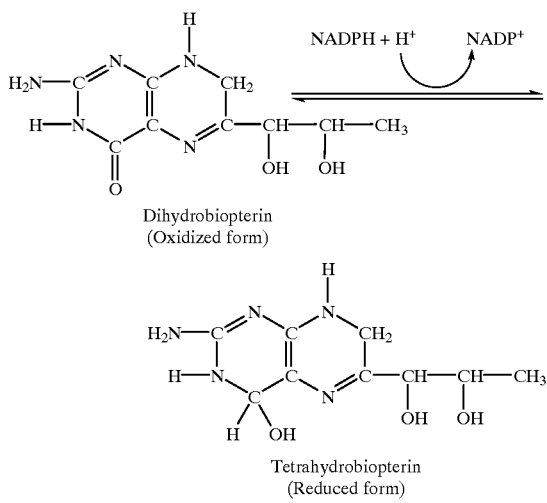

Dihydrobiopterin
(Oxidized form)

Tetrahydrobiopterin
(Reduced form)

In proteins made of combined amino acids, the alpha-carboxyl group of one amino acid is joined to the alpha-amino group of another amino aced by a peptide bond. The formation of a dipeptide from two amino acids is by loss of a water molecule. The equilibrium of this reaction lies far on the side of hydrolysis rather than synthesis. Hence, the biosynthesis of peptide bonds requires an input of free energy, whereas their hydrolysis is thermodynamically the reverse.

In the development of protein, many amino acids are joined by peptide bonds to form a polypeptide chain, which is an unbranched structure. A polypeptide chain has direction because its building blocks have different ends, namely the alpha-amino and the alpha carboxyl groups. By convention, the amino end is taken to be the beginning of a polypeptide chain. The sequence of amino acids in a polypeptide chain is written starting with the amino terminal residue.

A polypeptide chain consists of a regularly repeating part called the main chain and a variable part, comprising a distinctive side chain. In some proteins, a few side chains are cross-linked by disulfide bonds. These crosslinks are formed by the oxidation of cysteine residues. Resulting disulfide is called cysteine. No other co-valent crosslinks are generally found in proteins. Polypeptide chains are the basis of the cell walls of all cells of all living organisms.

Since the polypeptide chain is made up of molecules containing many double bonds and many sulfur bonds, the chain may be broken by a compound of high redox capacity. Chlorine dioxide is known as having one of the highest redox capacities of any of the compounds known to man. Thus, exposing individual amino acids or exposing the polypeptide chain of a dead cell to chlorine dioxide makes it an easy target for its disintegration.

The body fluids, such as saliva or vaginal fluid of animals, including humans, contain many organic compounds. Some of these are glycoproteins which contain atoms associated with double bonds and, like amino acids, are susceptible to degradation by chlorine dioxide. The degradation by-products from dead epithelial cells, dead bacteria and food debris residues form a pool of amino acids which are used for the nutrition of microbial populations.

The removal of these amino acids and glycoproteins by oxygenation would inhibit the growth of microorganisms. The bacteria would lack the building blocks to make new proteins. If daughter cells cannot be made because of a lack of proteins, then the numbers of bacteria in a given environment would be progressively diminished. To reduce the numbers of bacteria is an accepted way to treat infections.

The novelty of this invention is to reduce the availability of amino acids and/or glycoproteins in a given environment. It is not to create a toxicity in either the bacteria or host but rather a change in a local environment wherein bacteria are deprived of the amino acid building blocks for protein formation necessary for microorganisms to produce daughter cells.

Research of Amino Acids and Chlorine Dioxide Interaction

Chlorine dioxide is capable of degrading amino acids. The work of Lynch and coworkers showed that cysteine and methionine are degraded into pyruvate in the presence of chlorine dioxide. (Lynch E, Sheerin A, Claxson A W D, Atherton M D, Rhodes C J Silwood C J L, Naughton D P, Grootveld M. There were multicomponent spectroscopic investigations of salivary antioxidant consumption by an oral rinse preparation containing the stable free radical species chlorine dioxide ($ClO_2$). *Free Rad Res* 1997; 26:209–234.) The chemical change was documented using nuclear magnetic spin resonance. Grootveld et al studied microbial population in dental students which showed when they used chlorine dioxide in an oral rinse, the microbial counts were reduced. (Grootveld M, Silwood C, Lynch E. Ability of oral health care products to alleviate oral malodour. *J. Dent Res* (IADR Absts) 1997; #289:50.) Thus, the presence of chlorine dioxide will alter the milieux in the mouth by the degradation of glycoproteins and the removal of amino acids. This will inhibit bacterial growth and by doing so, can inhibit the numbers of bacteria present in the body fluids.

Amino acids are the essential building blocks for protein formation for cell walls. Protein is a requirement for all living creatures. Without the building blocks of amino acids, there is no protein and no life. Chlorine dioxide oxidatively consumes amino acids thus altering them into other compounds, primarily pyruvate or glutamate. Thus, the absence of amino acids as building blocks for life creates an environment which prevents the growth of microorganisms.

In cavities such as the human mouth or vagina, the numbers of bacteria are in the billions. They divide and make two daughter cells, usually every 20 to 40 minutes. To perpetuate the life of these organisms requires an enormous supply of amino acids. The use of the high redox capacity of an oxidative agent, such as $ClO_2$, can reduce the amount of available amino acids to become building blocks for protein production. The lack of available protein can prevent the maturation of the line of subsequent bacterial daughter cells. The reduction of the numbers of pathogenic organisms can prevent development of disease.

To test the known chemical reactions of amino acids with oxidizing agents, several studies were designed and conducted to determine the stability of nine essential and eight non-essential amino acids in the presence of chlorine dioxide at various time intervals. The studies and their results are tabulated in Studies 1–9B.

Since no adequate standard of relative efficiency of each of the various and natural aminotransaminases was available, it was decided to use the combination of chlorine dioxide with each individual amino acid without the assistance and facilitating benefit of the related transaminase for each separate amino acid. Thus, it is recognized that the effectiveness in vitro could be less than in vivo.

Following are conclusions that may be drawn from the studies set forth below.

Study 1 shows degradation of all the amino acids at their natural pH (as evaluated by liquid chromatography). The most important amino acids are cysteine and methionine in oral malodor and regarding DNA synthesis in production of new daughter cells. Methionine is the lead couplet on transfer ribonucleic acid (tRNA). Destruction of methionine in tRNA prevents the synthesis of protein. Oral maloder is the first step in the etiology of gingivitis and periodontitis. Inflammation of oral and other mucous membranes is caused by the penetration of bacterial toxins through surface epithelium into subepithelial connective tissue. The malodor compounds hydrogen sulfide ($H_2S$) derived from cysteine and methylmercaptam ($CH_3SH$) derived from methionine are well documented to be facilitating permeation agents allowing bacterial toxins through the intact healthy protective epithelium. Ratcliff, Perry A. and Johnson, Paul/Sequence of Events in the Pathogenesis of Gingivitis and Periodontitis (Accepted for publication by Journal of Periodontology).

Methionine which had a control baseline of 306 ppm which went to 89 ppm. Formylmethionine is the lead couplet of all bacterial tRNA, and its removal intercepts bacterial mitosis. It prevents bacterial secretion of peptides and enzymes. Cysteine went from 124 ppm to 1 ppm in five minutes. Phenylalanine went from 333 to 220 ppm in five minutes. Thus, if the $ClO_2$ is added to the amino acid in its natural pH milieu, the amino acid undergoes degradation. This denies 1) cell multiplication by deprivation of building blocks to produce and transfer new DNA for cell replication and 2) cell wall polypeptides.

Conclusion: $ClO_2$ can degrade amino acid building blocks for DNA synthesis and cell wall polypeptide chains.

Study #1

The Effect of Chlorine Dioxide on Amino Acid Stability

Purpose:
To determine the stability of nine essential and eight non-essential amino acids in the presence of chlorine dioxide at various time intervals.

Materials:
1. Amino Acid Standard H (Pierce Chemical Lot 97060265)
2. 5.3% Chlorine Dioxide
3. 10% Sodium Thiosulphate ($Na_2S_2O_3$)

Methods:
1. Five milliliter aliquots of amino acid standard (in 0.1 N HCl) were placed into 4 separate vials.
2. The stock chlorine dioxide concentration was confirmed via iodometric titration and 94 µl of 5.3% stock was added to each of three amino acid vials to bring the final concentration of chlorine dioxide to 0.10%.
3. The minimum amount of concentrated sodium thiosulphate needed to completely neutralize the chlorine dioxide was determined to be 1.0 ml of 10% concentrate.
4. The chlorine dioxide was neutralized at 1 minute for the first vial, 3 minutes for the second vial, and 5 minutes for the third vial.
5. To the untreated vial, 1.094 ml of a neutralized chlorine dioxide/sodium thiosulphate mixture was added as a control.
6. The resulting amino acid solutions were quantified via High Performance Liquid Chromatography.

Results

Visual Observations:
When the chlorine dioxide in the amino acid solution was neutralized, the solution turned to white opaque. The control solution remained clear, and the length of chlorine dioxide treatment was directly proportional to increased opaqueness of the solutions.

Amino Acid Stability:
The results showing amino acid stability in the presence of chlorine dioxide are shown in Table 1.

Method Limitations:
The concentration of amino acids were significantly lower in the control (0 min) sample than the expected values. This may be due to negative interferences(s) caused by the presence of a neutralized oxidant in the matrix. The exact nature of the interference(s) could not accurately be determined, and therefore could not be controlled. The amino acid concentrations may also have been subject to positive matrix interference(s) as some exhibited an increase over time.

Conclusion:
Based on the results, it appears that select amino acids were degraded when treated with a 0.1% chlorine dioxide solution when compared to the 0 minute control. It also appears that one or more positive matrix interferences may have been a factor for several amino acids, as their concentrations increased over time. However, most of these amino acids exhibited degradation after five minutes of treatment.

Results of Study #1

TABLE 1

AMINO ACID CONCENTRATION AFTER SPECIFIED TREATMENT

| Amino Acid Baseline 1 ml | | | | |
|---|---|---|---|---|
| Essential | | | | |
| Arginine | 357 | 340 | 310 | 230 | 35.574% |
| Histidine | 318 | 260 | 250 | 160 | 49.686 |
| Isoleucine | 269 | 200 | 210 | 170 | 36.803 |
| Leucine | 269 | 210 | 210 | 210 | 21.933 |
| Lysine | 300 | 230 | 240 | 200 | 33.333 |
| Methionine | 306 | 130 | 110 | 89 | 70.915 |
| Phenylalanine | 339 | 280 | 270 | 220 | 35.103 |
| Threonine | 244 | 190 | 190 | 180 | 26.230 |
| Tryptophan | | | | | |
| Valine | 240 | 180 | 190 | 150 | 37.500 |
| Nonessential | | | | | |
| Alanine | 183 | 150 | 150 | 140 | 23.497% |
| Aspartic acid | 273 | 240 | 230 | 240 | 12.088 |
| Cysteine | 124 | 3 | 2 | 1 | 99.194 |
| Glutamic acid | 302 | 260 | 260 | 270 | 10.695 |
| Glycine | 287 | 130 | 120 | 92 | 67.944 |
| Proline | 236 | 210 | 200 | 220 | 6.780 |
| Serine | 215 | 160 | 160 | 120 | 44.186 |
| Tyrosine | 316 | 310 | 290 | 230 | 26.445 |

Study 2 is a repeat of Study 1 wherein the pH was adjusted to 6.5, which is the pH of RetarDex a trademark of Rowpar Pharmaceuticals, Inc., oral rinse and the pH of a healthy mouth. There are differences in reactivity of cysteine and methionine in a healthy oral environment vs. a more acid environment. Also, there was no change in tryptophan.

Conclusion: Reaffirmation of findings in Study 1.

Study #2

The Effect of Chlorine Dioxide in Amino Acid Stability

Purpose:
To determine the stability of amino acids in the presence of chlorine dioxide at various time intervals.

Materials:
1. L-Amino acids, Sigma catalog No. LAA-21, lot No. 47H9006

2. 5.3% Chlorine Dioxide
3. 10% Sodium Thiosulphate ($Na_2S_2O_3$)

Methods:

1. A stock amino acid solution was prepared in de-ionized water to contain 0.1% of each amino acid and the pH adjusted to 6.5 with IN hydrochloric acid or 1N sodium hydroxide.
2. Five-milliliter aliquots of the amino acid solution were placed into 5 16×125 mm test tubes.
3. The stock chlorine dioxide concentration was confirmed via iodometric titration and 94 $\mu$l of 5.3% stock was added to each of three amino acid vials to bring the final concentration of chlorine dioxide to 0.10%.
4. The minimum amount of concentrated sodium thiosulphate needed to completely neutralize the chlorine dioxide was neutralized at 1 minute for the first vial, 3 minutes for the second vial, and 5 minutes for the third vial.
5. The chlorine dioxide was neutralized at 1 minute for the first vial, 3 minutes for the second vial, and 5 minutes for the third vial.
6. To one untreated vial, 1.094 ml of a neutralized chlorine dioxide/sodium thiosulphate mixture was added as Time 0. 1.094 ml of de-ionized water added to the second untreated tube as a control.
7. The resulting amino acid solutions were quantified via High Performance Liquid Chromatography.

Results:

Amino Acid Stability:

The results showing amino acid stability in the presence of chlorine dioxide are shown in Table 2.

TABLE 2

Amino Acid Concentrations When Treated with 0.1% Chlorine Dioxide

| Amino Acid | Control | Amino Acid Concentrations (%) After Specified Treatment Times | | | |
| --- | --- | --- | --- | --- | --- |
| | | 0 min. | 1 min. | 3 min. | 5 min. |
| Alanine | 0.45 | 0.46 | 0.43 | 0.43 | 0.44 |
| Arginine | 0.36 | 0.37 | 0.41 | 0.43 | 0.44 |
| Aspartic Acid | 0.51 | 0.55 | 0.46 | 0.46 | 0.48 |
| Cysteine | 0.22 | 0.07 | 0.01 | 0.01 | 0.01 |
| Glutamic Acid | 0.51 | 0.54 | 0.51 | 0.52 | 0.54 |
| Glycine | 0.66 | 0.65 | 0.61 | 0.61 | 0.64 |
| Histidine | 0.34 | 0.35 | 0.30 | 0.28 | 0.30 |
| Hydroxyproline | 0.47 | 0.84 | 0.71 | 0.71 | 0.72 |
| Isoleucine | 0.44 | 0.44 | 0.41 | 0.42 | 0.43 |
| Leucine | 0.45 | 0.45 | 0.42 | 0.43 | 0.44 |
| Lysine | 0.38 | 0.39 | 0.35 | 0.35 | 0.36 |
| Methionine | 0.47 | 0.49 | 0.30 | 0.29 | 0.29 |
| Phenylalanine | 0.46 | 0.47 | 0.43 | 0.44 | 0.45 |
| Proline | 0.32 | 0.33 | 0.33 | 0.32 | 0.35 |
| Serine | 0.53 | 0.52 | 0.51 | 0.51 | 0.52 |
| Tryptophan | 0.06 | 0.06 | 0.06 | 0.06 | 0.06 |
| Threonine | 0.45 | 0.45 | 0.43 | 0.43 | 0.45 |
| Tyrosine | 0.46 | 0.46 | 0.43 | 0.43 | 0.43 |
| Valine | 0.46 | 0.46 | 0.43 | 0.42 | 0.43 |

STUDY 3

Experimental Design

The purpose of this study was to further evaluate the interaction of $ClO_2$ with each amino acid. This study was completed to evaluate the loss of $ClO_2$ after mixing with each amino acid. Stability was determined by quantity decrease of $ClO_2$ from baseline to 1, 3 and 5 minutes.

Materials 1. 21 L-Amino Acids (Sigma Chemical Co.)
2. $ClO_2$ (5% concentrated stock)
3. 1.0 N HCl
4. 0.0250 N Sodium Thiosulfate ($Na_2S_2O_3$)
5. 10% Potassium Iodide (K1)

Methods 1. 1.0% solution of each amino acid was prepared in deionized water.
2. The exact concentration of the stock $ClO_2$ solution was determined iodometrically.
3. 98 microliters of $ClO_2$ stock were added to 5.0 ml of each individual amino acid to yield a concentration of 0.10% stock.
4. The solution was slowly mixed for 1 minute and the residual $ClO_2$ was determined.
5. Subsequent challenges were performed for each amino acid, allowing the $ClO_2$ and the amino acid to mix for 3 minutes and 5 minutes prior to titration.
6. Deionized water was used for the 0 time point.
7. The pH of each amino acid solution was measured prior to the addition of the chlorine dioxide.

Results

The chlorine dioxide concentration of the concentrated stock was 5.11%. The 0 minute control was 0.0998% chlorine dioxide. The chlorine dioxide concentrations and percent decrease at 1, 3 and 5 minutes are shown on page 27.

Studies 1–3. When compared to baseline, select amino acids were degraded after 5 minutes or less when treated with an 0.1% chlorine dioxide solution. The greatest reduction was with cysteine and methionine. Since these two amino acids are major molecules in riboneucleic acid and in deoxyribonecleic acid and are part of the polypeptide chain which forms the cell wall of microorganisms, the potential availability of these building blocks should reduce the potential mitotic capacity of bacteria. Study #3 evaluated the quantity of loss of $ClO_2$ when mixed with each amino acid. This provided further proof of interaction between $ClO_2$ and this family of compounds.

Study #3

Chlorine Dioxide Stability in L-Amino Acids

Purpose:

To determine the stability of $ClO_2$ in 21 L-amino acids at 1, 3, and 5 minutes.

Materials 1. 21 L-Amino Acids (Sigma Chemical Company)
2. $ClO_2$ (5% concentrated stock)
3. 1.0N HCl
4. 0.0250 N Sodium Thiosulphate ($Na_2S_2O_3$)
5. 10% Potassium Iodide (K 1)

Methods

1. A 1.0% solution of each amino acid was prepared in deionized water.
2. The exact concentration of the stock $ClO_2$ solution was determined iodometrically.
3. Ninety-eight microliters of $ClO_2$ stock were added to 5.0 ml of each individual amino acid to yield a concentration of 0.10%.
4. The solution was slowly mixed for one minute and the residual $ClO_2$ was determined.
5. Subsequent challenges were performed for each amino acid, allowing the $ClO_2$ and the amino acid to mix for 3 minutes and 5 minutes prior to titration.
6. Deionized water was used for the 0 time point.

7. The pH of each amino acid solution was measured prior to the addition of the chlorine dioxide.

Results

The chlorine dioxide concentration of the concentrated stock was 5.11%. The 0 minute control was 0.0998% chlorine dioxide. The chlorine dioxide concentrations and percent decrease at 1, 3 and 5 minutes are as follows:

TABLE 3

Chlorine Dioxide Concentrations and Percent Decrease

| L-Amino Acids | pH | 1 min | % Decrease | 3 min | % Decrease | 5 min | % Decrease |
|---|---|---|---|---|---|---|---|
| Alanine | 5.3 | 0.0962 | 3.6 | 0.0962 | 3.6 | 0.0962 | 3.6 |
| Arginine | 5.3 | 0.0932 | 6.6 | 0.0932 | 6.6 | 0.0928 | 7.0 |
| Asparagine | 3.7 | 0.0972 | 2.6 | 0.0962 | 3.6 | 0.0972 | 2.6 |
| Aspartic Acid | 2.8 | 0.0975 | 2.3 | 0.962 | 3.6 | 0.0958 | 4.0 |
| Cysteine | 3.7 | 0.0912 | 8.6 | 0.0925 | 7.3 | 0.0925 | 7.3 |
| Glutamic Acid | 2.9 | 0.0978 | 2.0 | 0.0958 | 4.0 | 0.0958 | 4.0 |
| Glutamine | 3.8 | 0.0982 | 1.6 | 0.0952 | 4.6 | 0.0958 | 4.0 |
| Glycine | 5.1 | 0.0968 | 3.0 | 0.0965 | 3.3 | 0.0958 | 4.0 |
| Histidine | 3.5 | 0.0978 | 2.0 | 0.0972 | 2.6 | 0.0975 | 2.3 |
| Hydroxyproline | 4.7 | 0.0975 | 2.3 | 0.0975 | 2.3 | 0.0978 | 2.0 |
| Isoleucine | 5.0 | 0.0978 | 2.0 | 0.0975 | 2.3 | 0.0972 | 2.6 |
| Leucine | 5.0 | 0.0952 | 4.6 | 0.0958 | 4.00 | 0.0958 | 4.0 |
| Lysine | 5.2 | 0.0985 | 1.3 | 0.0978 | 2.0 | 0.972 | 2.6 |
| Methionine | 4.9 | 0.0787 | 21.1 | 0.0793 | 20.5 | 0.0793 | 20.5 |
| Phenylalanine | 5.0 | 0.0985 | 1.3 | 0.0978 | 2.0 | 0.0978 | 2.0 |
| Proline | 5.5 | 0.0968 | 3.0 | 0.0975 | 2.3 | 0.0982 | 1.6 |
| Serine | 5.1 | 0.0982 | 1.6 | 0.0982 | 1.6 | 0.0975 | 2.3 |
| Threonine | 5.0 | 0.0975 | 2.3 | 0.0975 | 2.3 | 0.0978 | 2.0 |
| Tryptophan | 4.9 | 0.0516 | 48.3 | 0.0529 | 47.0 | 0.0522 | 47.7 |
| Tyrosine | 5.5 | 0.0995 | 0.3 | 0.0992 | 0.6 | 0.0992 | 0.6 |
| Valine | 5.8 | 0.0998 | 0 | 0.0988 | 0 | 0.0992 | 0.6 |

Study 4 is to evaluate tryptophan which is an important amino acid in the formation of protein from amino acids. Tryptophan was exposed to $ClO_2$ for determination of the changes that might take place. Tryptophan untreated was the control Conclusion: The experimental period of up to 5 minutes showed progressive degradation of tryptophan by $ClO_2$ in comparison to the control.

Study #4

The Effect of Chlorine Dioxide on Acidified Tryptophan

Purpose:

To determine the stability of acidified tryptophan in the presence of chlorine dioxide at various time intervals.

Materials:
1. Tryptophan
2. 5.3% Chlorine Dioxide
3. 10% Sodium Thiosulphate ($Na_2S_2O_3$)

Methods:
1. Five-milliliter aliquots of a tryptophan standard (in 0.1 N HCl) were placed into 5 separate vials.
2. The stock chlorine dioxide concentration was confirmed via iodometric titration and 94 μl of 5.3% stock was added to each of three amino acid vials to bring the final concentration of chlorine dioxide to 0.10%.
3. The minimum amount of concentrated sodium thiosulphate needed to completely neutralize the chlorine dioxide was determined to be 1.0 ml of 10% concentrate.
4. The chlorine dioxide was neutralized at 1 minute for the first vial, 3 minutes for the second vial, and 5 minutes for the third vial.
5. For Time 0, 1.094 ml of a neutralized chlorine dioxide/sodium thiosulphate mixture was added as a control.
6. An untreated tryptophan solution was analyzed as a control.

Results:

The results are shown in Table 4.

TABLE 4

Results Showing the Effect of Chlorine Dioxide on Acidified Tryptophan

| | Tryptophan (PPM) | | | | |
|---|---|---|---|---|---|
| Amino Acid | Control | 0 min. | 1 min. | 3 min. | 5 min. |
| Tryptophan | 1,600 | 1,100 | 900 | 600 | 400 |

Study 5 was to show the effect of $ClO_2$ on the bacterial growth characteristics of tryptic soy broth (TSB) which contains amino acids. TSB is a culture medium for gram positive bacteria. This study was to determine if the change that occurred was a result of the exposure of bacteria to TSB plus the 0.1% $ClO_2$ versus TSB without the 0.1 $ClO_2$ formulation. Would there be a change in the growth medium rather than a change on the bacteria? Consequently, prior to inoculation with the test bacteria, the growth medium was treated with $ClO_2$ and then the $ClO_2$ removed from the medium by the thiosulfate procedure as used in the earlier experiments. The results of this study showed that when TSB was treated with $ClO_2$ there was a very high loss of bacterial growth between the untreated control and treated TSB. Colony forming units were over two million in the control, and the experimental group after treatment with $ClO_{27}$ had less than 10% bacterial growth.

Conclusion: $ClO_2$ degrades amino acids in the growth medium, denying building blocks to produce bacterial daughter cells.

Study #5

Effect of Chlorine Dioxide on the Growth Characteristics of Tryptic Soy Broth

Purpose:

To determine the effect of chlorine dioxide on the growth characteristics of Tryptic Soy Broth (TSB) using *Streptococcus mutans*.

Materials:

1. Tryptic Soy Broth (TSB), formula per liter:
   a. Pancreatic digest of casein    17.0 g
   b. Sodium chloride                 5.0 g
   c. Papaic digest of soybean meal   3.0 g
   d. $K_2HPO_4$                      2.5 g
   e. Glucose                         2.5 g
2. *Streptococcus mutans*, ATCC#25175
3. Plate Count Agar
4. Chlorine dioxide Methods:
1. TSB was seeded with 0.1% and incubated for 24 hours at 35° C. Subsequent to incubation the residual chlorine dioxide was determined iodometrically.
2. Three ten-milliliter aliquots of TSB were spiked with 0.011% chlorine dioxide, the amount consumed in 24 hours, incubated for 24 hours at 35° C. and inoculated with 3,600 colony forming units of S. mutans. Three 10-milliliter aliquots of non-chlorine dioxide treated TSB were inoculated as a control.

Results:

TABLE 5

| Solution | Culture Media | S. mutans (CFU per milliliter) |
|---|---|---|
| 1 | TSB | 360,000,000 |
| 2 | TSB | 400,000,000 |
| 3 | TSB | 510,000,000 |
| Average | TSB | 420,000,000 |
| 4 | TSB + 0.011% ClO2 | 65,000,000 |
| 5 | TSB + 0.011% ClO2 | 9,000,000 |
| 6 | TSB + 0.011% ClO2 | 46,000,000 |
| Average | TSB + 0.011% ClO2 | 40,000,000 |

Study 6 verifies the same observations as in Study #5 using tryptic soy agar and *Streptococcus mutans* as a marker. This demonstrates that you can obliterate the growth of *S. mutans* with Conclusion: Inasmuch as *S. mutans* is generally recognized as a major cause of dental decay, this would suggest that dental decay can be arrested by the use of a $ClO_2$ 0.1% solution by amino acid deprivation.

Study #6

Purpose:

To determine the effect of 0.1% chlorine dioxide on tryptic soy agar's ability to support bacterial growth.

Materials:

1. 10 g. Tryptic soy agar base in 238 ml of deionized water
2. 12.5 ml sheep blood per aliquot
3. 5.7% stock chlorine dioxide ($ClO_2$)
4. 10% Sodium thiosulphate ($Na_2S_2O_3$)
5. *Streptococcus mutans* ATCC #25175
6. 500 ml Erlenmeyer flasks
7. 30 petri plates
8. Sterile deionized water
9. Plate count agar Methods:

A suspension of *S. nutans* was prepared in Butterfield's buffer and the concentration of viable bacteria determined utilizing the standard plate count method.

Three aliquots of Tryptic soy agar base were prepared and cooled to 50° C. One aliquot was treated with stock chlorine dioxide to yield a 0.1% concentration (4.4 ml) for 30 seconds. After 30 seconds the chlorine dioxide was neutralized with 10% sodium thiosulphate (45 ml). The second aliquot was treated with the same volume of 10% sodium thiosulphate needed to neutralize the 0.01% $ClO_2$. The third aliquot did not receive any chemical treatment and was labeled as the control.

Subsequently each aliquot was supplemented with 5% sheep blood and poured into petri dishes.

Solidified plates from each aliquot were inoculated with *S. mutans* stock to yield ≅60 CFU/plate. The plates were incubated at 35° C. for 72 hours. At 24 hour intervals, the colonies were enumerated and described by colony presentation.

Results:

The chlorine dioxide and sodium thiosulphate treated blood agar plates did not support the growth of *Streptococcus mutans*.

TABLE 6

| Agar tested | Colony size (24 hr.) | No. of colonies (24 hr.) | Colony size (48 hr.) | No. of colonies (48 hr.) | Colony size (72 hr.) | No. of colonies (72 hr.) |
|---|---|---|---|---|---|---|
| Control (No treatment) | 1 mm | 12 | 1 mm | 145 | 1 mm | 145 |
| $ClO_2$ treated agar | N/A | 0 | N/A | 0 | N/A | 0 |
| $Na_2S_2O_3$ treated agar | N/A | 0 | N/A | 0 | N/A | 0 |

Discussion

Tryptic soy agars treated with chlorine dioxide and neutralized with sodium thiosulphate, and only sodium thiosulphate treated agars prior to the addition of 5% sheep blood did not provide a suitable medium for *Streptococcus mutans* proliferation.

Study 7: The FDA requires the addition of calf serum to TSB when one is attempting to simulate the oral environment. This is because TSB does not have the full amino acid content of human saliva which largely exists in calf serum. Accordingly, Study 6 repeats Study 5 with the substitution of calf serum instead of TSB as a growth medium. It showed that with a common time exposure, untreated TSB had 910,000 colony forming units (CFU) of the test organisms, *S. mutans*, whereas the TSB treated with $ClO_2$ had an average of 860 CFU. This suggests that the use of $ClO_2$ results in a reduction of amino acid nutrients for the formation of bacterial daughter cells.

Conclusion: In the synthesis of protein and DNA, the reduction in critical amino acids is sufficient to prevent the growth of new organisms due to the lack of its nutrient base.

Study #7

Effect of Chlorine Dioxide on the Growth Characteristics of Tryptic Soy Broth (TSB) and Calf Serum Purpose:

To determine the effect of chlorine dioxide on the growth characteristics of Tryptic Soy Broth (TSB) and calf serum using *Streptococcus mutans*.

Materials:

| | |
|---|---|
| 1. Tryptic Soy Broth (TSB), formula per liter: | |
| a. Pancreatic digest of casein | 17.0 g |
| b. Sodium chloride | 5.0 g |
| c. Papaic digest of soybean meal | 3.0 g |
| d. $K_2HPO_4$ | 2.5 g |
| e. Glucose | 2.5 g |
| 2. Calf serum | |
| 3. *Streptococcus mutans*, ATCC#25175 | |
| 4. Plate Count Agar | |
| 5. Chlorine dioxide | |

Methods

1. TSB, 5 ml, was seeded with 0.1% chlorine dioxide, incubated for 24 hours at 35° C. and any residual chlorine dioxide neutralized with 1 ml 10% sodium thiosulphate. Portions of each test solutions were aliquoted into each of three sterile 16×125-mm test tubes. As a control, a portion of TSB was also treated with neutralized sodium thiosulphate as above.

2. Testing of serum was handled in a similar manner, except TSB was substituted with calf serum.

3. Each of the aliquots was seeded with approximately 100 CFU of *S. mutans*, incubated for 24 hours at 35° C. and enumerated via aerobic plate count techniques.

Results

TABLE 7

| No. | Growth Matrix | ClO$_2$ | S. mutans (CFU per milliliter) | | | |
|---|---|---|---|---|---|---|
| | | | 1 | 2 | 3 | Average |
| 1 | Tryptic Soy Broth | No | 2,300,000 | 2,000,000 | 2,100,000 | 2,100,000 |
| 2 | Tryptic Soy Broth | Yes | 760 | 870 | 940 | 860 |
| 3 | Calf Serum | No | 780,00 | 840,000 | 1,100,000 | 910,000 |
| 4 | Calf Serum | Yes | <10 | <10 | <10 | <10 |

Study 8 was a control where the amino acids had received sodium thiosulfate only, with no addition of ClO$_2$. Inasmuch as the thiosulfate was used to neutralize the ClO$_2$ in previous studies, there was a need to document that the amino acids were not affected by the thiosulfate, only by the ClO$_2$.

Conclusion: the nature of change was documented to be the result of the ClO$_2$ and not the thiosulfate neutralizing agent

Study #8

Purpose:
To determine the effect of sodium thiosulphate on amino acid recovery.

Materials:
1. Amino acids: cystine, methionine, tryptophan
2. Sodium thiosulphate, 10%

Methods:
A solution of the three amino acids was prepared in deionized water at a concentration of 2,750 ppm and adjusted to pH 6.5. The solution was aliquoted into two test tubes. One milliliter of deionized water was added to the first tube and 1 milliliter of 10% sodium thiosulphate added to the second. The samples were analyzed for amino acid content by Woodson-Tenent Laboratories in Des Moines, Iowa.

Results:

TABLE 8

| Amino Acid | Amino Acids + Water | Amino Acids + Sodium thiosulphate |
|---|---|---|
| Cystine | 3,200 | 2,700 |
| Methionine | 3,000 | 3,000 |
| Tryptophan | 2,500 | 2,400 |

Studies 9and 9B: Inflammation of the gingiva is caused by bacterial toxin which is a lipopolysaccharide (LPS). The purpose of these studies was to evaluate the effect of ClO$_2$ on LPS. The reduction of inflammation shown in clinical studies of ClO$_2$ oral rinse use by earlier investigators came not because of the elimination of LPS by ClO$_2$ but rather because of the elimination of the bacteria that produced the LPS.

Conclusion: The effect of ClO$_2$ on LPS was absent or negligible up to five hours. Thus beneficial oral changes by use of ClO$_2$ oral rinse reported by Chapek et al. were from reduction of numbers of bacteria and not LPS neutralization.

Study #9A

Effect of Chlorine Dioxide in Lipopolysaccharide

Purpose:
To determine the effect of 0.1% chlorine dioxide on purified Lipopolysaccharide of E. coli 055:B5.

Materials:
1. Endotoxin, purified Lipopolysaccharide (LPS) of E. coli 055:B5, manufactured by Charles River Endosafe, Lot No. 64852.
2. Limulus Amebocyte Lysate (LAL) test kit, manufactured by Charles River Endosafe, Lot No. L1042L, Exp 10/2000, 0.25 EU/ml.
3. Sodium thiosulphate, 20% prepared in endotoxin free water.
4. Chlorine dioxide stock solution, 5.3%.
5. LAL reagent water, Lot No. L72881, Exp 10/99.

Methods:
The purified LPS was reconstituted with 10 ml endotoxin free water to yield a concentration of 100,000 EU per milliliter. The endotoxin suspension was aliquoted into ten depyrogenated test tubes (13×100 mm), 1 ml per tube and the temperature equilibrated to 37° C. Each of the ten aliquots were treated with 19 ul of 5.3% chlorine dioxide to yield a final concentration of 0.1% chlorine dioxide. Each of the solutions was allowed to react as shown in Table 9A below. After the reaction time, 100 ul of 20% sodium thiosulphate was added to the solution to neutralize any unreacted chlorine dioxide. For the zero time point, the chlorine dioxide was neutralized with sodium thiosulphate prior to addition to the endotoxin stock solution. After the reaction period, each tube was quantified for endotoxins employed the LAL test kit.

TABLE 9A

| No. | Reaction Time (Min) | 5.3% ClO$_2$ (ul) | 20% Na$_2$S$_2$O$_2$ | Endotoxin Stock (ml) |
|---|---|---|---|---|
| 1 | 0 | 19 | 100 | 1 |
| 2 | 1 | 19 | 100 | 1 |
| 3 | 3 | 19 | 100 | 1 |
| 4 | 5 | 19 | 100 | 1 |
| 5 | 30 | 19 | 100 | 1 |
| 6 | 60 | 19 | 100 | 1 |
| 7 | 120 | 19 | 100 | 1 |
| 8 | 180 | 19 | 100 | 1 |
| 9 | 240 | 19 | 100 | 1 |
| 10 | 300 | 19 | 100 | 1 |

Quality Control
1. Endotoxin free water
2. Endotoxin free water+100 ul 20% sodium thiosulphate
3. Endotoxin free water+100 ul 20% sodium thiosulphate+19u 5. 3% chlorine dio
4. Endotoxin free water+19ul 5.3% chlorine dioxide
5. Endotoxin free water+100 ul 20% sodium thiosulphate+19ul 5.3% chlorine dio endotoxin.

Results
The results are shown in Table 9AA. Chlorine dioxide, 0.1% did not demonstrate measurable effect on the Lipopolysaccharide within the five hour reaction time.

TABLE 9AA

Results Showing the Effect of 0.1% Chlorine Dioxide on Lipopolysaccharide of E. coli 055:B5

| No. | Reaction Time (Min) | Chlorine Dioxide (%) | Endotoxin (EU/ml) |
|---|---|---|---|
| 1 | 0 | 0.1 | ≧100,000 |
| 2 | 1 | 0.1 | ≧100,000 |
| 3 | 3 | 0.1 | ≧100,000 |

TABLE 9AA-continued

Results Showing the Effect of 0.1% Chlorine Dioxide on
Lipopolysaccharide of *E. coli* 055:B5

| No. | Reaction Time (Min) | Chlorine Dioxide (%) | Endotoxin (EU/ml) |
|---|---|---|---|
| 4 | 5 | 0.1 | ≧100,000 |
| 5 | 30 | 0.1 | ≧100,000 |
| 6 | 60 | 0.1 | ≧100,000 |
| 7 | 120 | 0.1 | ≧100,000 |
| 8 | 180 | 0.1 | ≧100,000 |
| 9 | 240 | 0.1 | ≧100,000 |
| 10 | 300 | 0.1 | ≧100,000 |
| Control 1 | 0 | 0 | <0.25 |
| Control 2 | 0 | 0 | <0.25 |
| Control 3 | 0 | 0.1 | <0.25 |
| Control 4 | 0 | 0.1 | <0.025 |
| Control 5 | 0 | 0.1 | ≧0.25 |

Study #9B

Effect of Chlorine Dioxide on Lipopolysaccharide

Purpose:

To determine the effect of 0.1% chlorine dioxide on purified Lipopolysaccharide of *E. coli* 055:B5.

Materials:

1. Endotoxin, purified Lipopolysaccharide (LPS) of *E. coli* 055:B5, manufactured by Charles River Endosafe, Lot No. 64852.
2. Limulus Amebocyte Lysate (LAL) test kit, manufactured by Charles River Endosafe, Lot No. L, 042L, Exp 10/2000, 0.25 EU/ml.
3. Sodium thiosulphate, 20%, prepared in endotoxin free water.
4. Chlorine dioxide stock solution, 5.3%
5. LAL reagent water, Lot No. L72881, Exp 10/99.

Methods:

The purified LPS was reconstituted with 100 ml endotoxin free water to yield a concentration of 10,000 EU per milliliter. The endotoxin suspension was aliquoted into ten depyrogenated test tubes (13×100 mm), 1 ml per tube and the temperature equilibrated to 37° C., Each of the ten aliquots were treated with 19 ul of 5.3% chlorine dioxide to yield a final concentration of 0.1% chlorine dioxide. Each of the solutions was allowed to react as shown in Table 9B below. After the reaction time, 100 ul of 20% sodium thiosulphate was added to the solution to neutralize any unreacted chlorine dioxide. For the zero time point, the chlorine dioxide was neutralized with sodium thiosulfate prior to addition to the endotoxin stock solution. After the reaction period, each tube was quantified for endotoxins employed the LAL test kit.

TABLE 9B

| No. | Reaction Time (Hour) | 5.3% $ClO_2$ (ul) | 20% $Na_2S_2O_3$ | Endotoxin Stock (ml) |
|---|---|---|---|---|
| 1 | 0 | 19 | 100 | 1 |
| 2 | 1 | 19 | 100 | 1 |
| 3 | 12 | 19 | 100 | 1 |
| 4 | 24 | 19 | 100 | 1 |

Quality Control

1. Endotoxin free water
2. Endotoxin free water+100 ul 20% sodium thiosulphate
3. Endotoxin free water+100 ul 20% sodium thiosulphate+19 ul 5.3% chlorine dioxide
4. Endotoxin free water+19 ul 5.3% chlorine dioxide
5. Endotoxin free water+100 ul 20% sodium thiosulphate+19 ul 5.3% chlorine dioxide+endotoxin.

Results

The results are shown in Table 9BB. Chlorine dioxide, 0.1% did not demonstrate any measurable effect of the Lipopolysaccharide within the 24 hours reaction time

TABLE 9BB

Results Showing the Effect of 0.1% Chlorine Dioxide on Lipopolysaccharide of *E. coli* 055:B5.

| No. | Reaction Time (Hour) | Chlorine Dioxide (%) | Endotoxin (EU/ml) |
|---|---|---|---|
| 1 | 0 | 0.1 | ≧10,000 |
| 2 | 1 | 0.1 | ≧10,000 |
| 3 | 12 | 0.1 | ≧10,000 |
| 4 | 24 | 0.1 | ≧10,000 |
| Control 1 | 0 | 0 | <0.25 |
| Control 2 | 0 | 0 | <0.25 |
| Control 3 | 0 | 0.1 | <0.25 |
| Control 4 | 0 | 0.1 | <0.25 |
| Control 5 | 0 | 0.1 | ≧0.25 |

EXAMPLE 1

Hypothetically, a composition having chlorine dioxide was mixed with Amino Acid Standard H to obtain a final concentration of chlorine dioxide of 0.01%. It is predicted that the amino acids will be degraded within one minute and significantly degraded within five minutes of subjecting the amino acids to the chlorine dioxide.

EXAMPLE 2

Hypothetically, a composition having chlorine dioxide was mixed with Amino Acid Standard H to obtain a final concentration of chlorine dioxide of 0.3%. It is predicted that the amino acids will be degraded within one minute and significantly degraded within five minutes of subjecting the amino acids to the chlorine dioxide.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

We claim:

1. A method for oxidatively consuming amino acids selected from the group consisting of cysteine, methionine, tryptophan, argenine, histidine, isoleucine, leucine, lysine, phenylalanine, threonine, valine, alanine, aspartic acid, glutamic acid, glycine, proline, serine and tyrosine present upon the internal and external tissue surfaces of animals and man to reduce the presence of microorganisms by reducing the building blocks for protein formation necessary for the microorganisms to produce daughter cells, said method comprising the step of applying to the tissue surfaces a composition comprising a topical preparation containing chlorine dioxide in a concentration in the range of about 0.01% to about 0.3%.

2. The method as set forth in claim 1 wherein said step of applying is carried out for at least 5 seconds.

3. A method for reducing the growth of microorganisms present at an infection site, said method comprising the step of degrading amino acids and glycoproteins present at the infection site by applying a composition comprising a topical preparation containing chlorine dioxide in a concentration in the range of about 0.01% to a about 0.3% to oxidatively consume the amino acids and glycoproteins present and deprive the microorganisms of building blocks for protein formation necessary for the microorganisms to produce daughter cells.

4. A method for cleaning a dental prosthetic device, said method comprising the step of reducing the microbial growth associated with and attached to the device by applying a composition comprising a topical preparation containing chlorine dioxide in a concentration in the range of about 0.01% to about 0.3% to oxidatively consume amino acids and glycoproteins present and reduce the building blocks for protein formation necessary for microorganisms to produce daughter cells.

5. A method for altering the amino acid milieux present in any of the oral, vaginal and other body cavities, said method comprising the step of oxidatively consuming the amino acids by applying to the selected cavity a composition comprising a topical preparation containing chlorine dioxide in a concentration in the range of about 0.01% to about 0.3%.

6. A method for inhibiting bacterial growth, said method comprising the step of applying to the location of bacterial growth a composition comprising a topical preparation containing chlorine dioxide in a concentration in the range of about 0.01% to about 0.3% to oxidatively consume amino acids and glycoproteins present and thereby reduce the building blocks for protein formation necessary for the bacteria to produce daughter cells.

7. A method for oxidatively consuming amino acids selected from the group consisting of cysteine, methionine, tryptophan, arginine, histidine, isoleucine, leucine, lysine, phenylalanine, threonine, valine, alanine, aspartic acid, glutamic acid, glycine, proline, serine and tyrosine present upon the internal and external tissue surfaces of animals and man to reduce the presence of microorganisms to produce daughter cells, said method comprising the step of suppressing tRNA to prevent synthesis of protein by applying to the tissue surfaces a composition comprising a topical preparation containing chlorine dioxide in a concentration in the range of about 0.01% to about 0.3%.

* * * * *